(12) United States Patent (10) Patent No.: US 7,247,306 B2
Fliss et al. (45) Date of Patent: Jul. 24, 2007

(54) BACTERIA STRAIN AND BACTERIOCIN PRODUCED THEREFROM

(75) Inventors: Ismail Fliss, Sainte-Foy (CA); Michel Desbiens, Gaspé (CA); Christophe Lacroix, Kilchberg (CH); Imane Tahiri, Québec (CA); Régis-Olivier Benech, Montréal (CA); Ehab Kheadr, Sainte-Foy (CA)

(73) Assignee: Universite Laval, Québec (CA)

( * ) Notice: Subject to any disclaimer, the term of this patent is extended or adjusted under 35 U.S.C. 154(b) by 0 days.

(21) Appl. No.: 10/834,886

(22) Filed: Apr. 30, 2004

(65) Prior Publication Data

US 2005/0245443 A1 Nov. 3, 2005

(51) Int. Cl.
*A61K 39/02* (2006.01)

(52) U.S. Cl. .............................. 424/234.1; 424/185.1; 424/190.1; 530/350; 435/243; 435/252.1; 514/12

(58) Field of Classification Search ............. 424/234.1, 424/185.1, 190.1; 435/243, 252.1; 536/23.7; 530/350; 514/12
See application file for complete search history.

(56) References Cited

U.S. PATENT DOCUMENTS

| 6,207,411 B1 | 3/2001 | Ross et al. |
| 6,855,518 B2 | 2/2005 | Berjeaud et al. |
| 2004/0214173 A1 | 10/2004 | Berjeaud et al. |
| 2005/0232910 A1 | 10/2005 | Berjeaud et al. |

FOREIGN PATENT DOCUMENTS

| EP | 453719 | 12/1994 |
| JP | 01 335597 | 4/2001 |
| KR | 1054081 A | 7/2001 |
| WO | WO 94/04682 | 3/1994 |
| WO | WO 96/26216 | 8/1996 |
| WO | WO 97/06811 | 2/1997 |
| WO | WO 97/23619 | 7/1997 |
| WO | WO 02/26059 | 4/2002 |

OTHER PUBLICATIONS

Brillet et al. (Letter in Appl. Microbiol. May 2003. 36: 288-292).*
Melvier et al. (Microbiology. 1998. 144: 2837-2844).*
Kaiser et al. (Applied Environ. Microbiol. 1996. 62 : 4529-4535).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Dicks et al (Current Microbiology. 1995. 31: 77-79).*
Benech R.-O. et al., 2002, Applied and Environmental Microbiology, vol. 68, No. 11, pp. 5607-5619.
Benech R.-O. et al., 2002, Applied and Environmental Microbiology, vol. 68, No. 8, pp. 3683-3690.
Bertrand N. et a., 2001, International Dairy Journal, vol. 11, pp. 953-960.
Bhugaloo-Vial P. et al., 1996, Applied and Environmental Microbiology, vol. 62, No. 12, pp. 4410-4416.
Daoudi L. et al., 2001, Appl. Microbiol. Biotechnol., vol. 56, pp. 114-119.
Herbin S. et al., 1997, Current Microbiology, vol. 35, pp. 319-326.
Holck A. et al., 1996, FEMS Microbiology Letters, vol. 136, pp. 163-168.
Laridi R. et al., 2003, International Dairy Journal, vol. 13, pp. 325-336.
Prioult G. et al., 2000, International Dairy Journal, vol. 10, pp. 627-633.
Quadri L. E. N. et al., 1994, The Journal of Biological Chemistry, vol. 269, No. 16, pp. 12204-12211.
Worobo R. W. et al., Journal of Bacteriology, vol. 177, No. 11 pp. 3143-3149.

* cited by examiner

*Primary Examiner*—Jennifer E. Graser
(74) *Attorney, Agent, or Firm*—Ogilvy Renault, LLP

(57) ABSTRACT

The present invention concerns an isolated bacteriocin, Divergicin M35, derived form *Carnobacterium divergens* M35. It also concerns a composition comprising an effective amount of Divergicin M35 and the use of that bacteriocin to kill or limit the proliferation of a microorganism.

6 Claims, 6 Drawing Sheets

```
                           SEQUENCE LISTING

<160> NUMBER OF SEQ ID NOS: 1

<210> SEQ ID NO 1
<211> LENGTH: 43
<212> TYPE: PRT
<213> ORGANISM: Carnobacterium divergens

<400> SEQUENCE: 1

Thr Lys Tyr Tyr Gly Asn Gly Val Tyr Cys Asn Ser Lys Lys Cys Trp
  1               5                  10                  15

Val Asp Trp Gly Thr Ala Gln Gly Cys Ile Asp Val Val Ile Gly Gln
             20                  25                  30

Leu Gly Gly Gly Ile Pro Gly Lys Gly Lys Cys
             35                  40
```

BACTERIA STRAIN AND BACTERIOCIN PRODUCED THEREFROM

BACKGROUND OF THE INVENTION (a) Field of the Invention

The present invention relates to a novel bacteriocin, divergicin M35, produced by the *Carnobacterium divergens* strain M35. The present invention also relates to a composition comprising an effective amount of divergicin M35 and the use of that bacteriocin to kill or limit the proliferation of a microorganism such as *L. monocytogenes*.

(b) Description of Prior Art

Lactic acid bacteria (LAB) are food-grade microorganisms used for the production of numerous fermented food products to improve their flavor, texture and shelf-life. LAB produce antibacterial compounds that include organic acids, diacetyl, hydrogen peroxide and bacteriocins, which are known to reduce food spoilage and growth or proliferation of pathogenic bacteria. Use of these naturally produced compounds as food bio-preservative agents has therefore gained increasing attention in the food industry and now represents a promising way to preserve food without chemical agents, especially in ready-to-use products. Bacteriocins may also find use in the preparation of products that are not submitted to sufficient thermal sterilization during their production, since they represent a risk of contamination by pathogenic bacteria such as *Listeria monocytogenes*, known in the art to be responsible for numerous worldwide outbreaks. The ability of *L. monocytogenes* to survive longer at refrigerated temperatures and at sodium chloride concentrations up to 10% makes it a serious health threat, particularly in lightly-preserved seafood.

LAB represent the predominant microbial population flora in low temperature stored products. Among LAB that produce antibacterial compounds and that can be used as food-preservative agent, *Carnobacteria* are particularly attractive since they show interesting physiological characteristics. Indeed, they grow at low temperatures, high sodium chloride concentration and limited carbohydrate concentration, they produce high-antilisterial bacteriocins and have lower acidifying capacities than other bacteriocin-producing LAB.

The prior art reports the isolation and characterization of numerous *Carnobacterium* bacteriocins such as carnobacteriocins BM1 and B2 (Quadri et al., 1994), divergicin LV13 (Worobo et al., 1995), divercin V41 (Métivier et al., 1998), divergicin 750 (Holck et al., 1996), piscicocin V1a (Bhugaloo-Vial et al., 1996) and carnocin CP5 (Herbin et al., 1997). Although those bacteriocins are known, they were not isolated for the particular purpose of preserving sea food products and their activity spectrum can vary significantly toward pathogen microorganisms. Moreover, only a few studies have reported characterization of bacteriocins from *Carnobacterium* species isolated from fish and especially those produced by *C. divergens* strains.

Thereofore, it would be desirable to be provided with a bacteriocin produced by a *Carnobacterium divergens* strain having anti-listerial activity and capable to grow under conditions encountered in the manufacture and preservation of sea-food products.

SUMMARY OF THE INVENTION

The present invention relates to a bacteriocin, divergicin M35, that comprises amino acid sequence SEQ. ID. NO: 1, a functional fragment or a functional variant thereof and a nucleic acid sequence encoding the above bacteriocin. The invention also relates to a bacteria that produce divergicin M35 and a method for producing and purifying the bacteriocin that comprises cultivating the bacteria.

The present invention also provides for the use of that bacteriocin to kill a bacteria or limit its proliferation and composition to be used for the same purpose that comprises an effective amount of the bacteriocin in association with a carrier.

For the purpose of the present invention the following terms are defined below.

The term "APT" is intended to mean all purpose medium with Tween®.

The term "ATCC" is intended to mean American Type and Culture Collection.

The term "LAB" is intended to mean Lactic acid bacteria.

The term "MRS" is intended to mean lactobacillus broth according to DeMan, Rogosa and Sharpe.

The term "PCR" is intended to mean polymerase chain reaction.

The term "TBS" is intended to mean tryptic soy broth.

DESCRIPTION OF THE PREFERRED EMBODIMENTS

Figure 1:
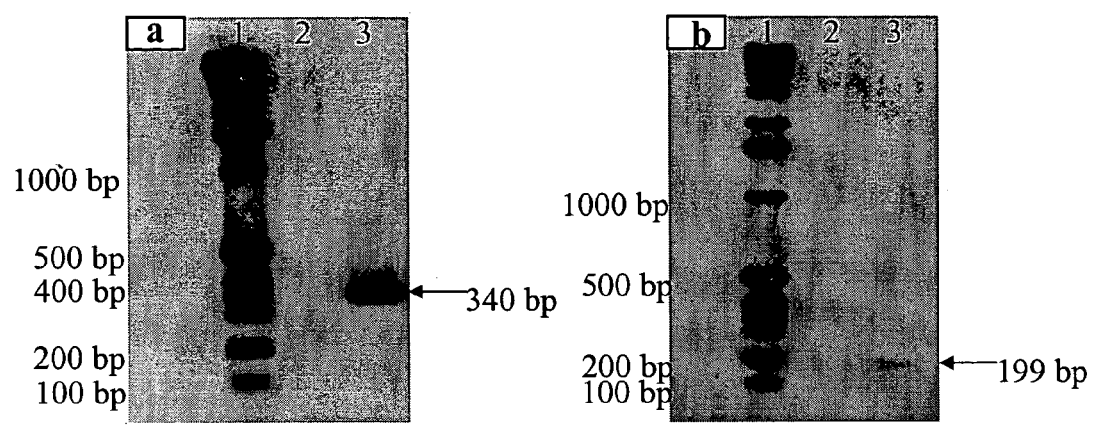
FIGS. 1a and 1b are the M35 strain genus and species assignment by PCR analyses.

The bacteriocin of the present invention is obtained from a *Carnobacterium divergens* strain isolated from sea food, and more particularly frozen smoked mussels, harvested in the St. Laurence River in Canada, namely the M35 strain. Consequently, the bacteriocin produced therefrom has been trivially named divergicin M35.

Since the bacteria producing divergicin M35 are found endogenously in the ecosystem of the St. Laurence River, the bacteria that produce the bacteriocin of the present invention may be wild-type bacteria that express an endogenous gene encoding SEQ. ID. NO:1, a functional fragment or a functional variant thereof. Particularly, the divergicin M35-expressing wild-type bacteria belong to the *Carnobacterium divergens* species and more particularly, belong to the strain registered at the International Depositary Authority of Canada under deposit number 050404-01.

A skilled artisan will understand that production of divergicin M35 is not restricted to endogenous expression of the bacteriocin by a wild-type bacterial strain. The bacteriocin of the present invention may be produced by a recombinant microorganism that properly expresses a functional divergicin M35. Any microorganism capable of producing divergicin M35 may be used and includes any microorganism species that does not express endogenously divergicin M35 and for which the genome has to be modified to express the bacteriocin of the present invention, such as yeasts, fungi and bacteria.

The bacteriocin of the present invention comprises a forty-three (43) amino acids sequence and has a molecular weight that ranges between 4,400 and 4,600 Da. However, divergicin M35 preferably has a molecular weight of 4518 Da, as determined by mass spectrometry. Amino acid sequence comparison with class IIa bacteriocin showed homology degrees varying form 51% with mundticin to 80.5% with divercin V41. Divergicin M35 has a high content of non-polar and small amino acids, which is characteristic to class IIa bacteriocins. Therefore, divergicin M35 was assigned to class IIa bacteriocins.

The inhibition spectrum of divergincin M35 is also related to the characteristic inhibition spectrum of class IIa bacteriocins. Indeed, the bacteriocin of the present invention is effective toward numerous bacterial microorganisms and particularly toward *Listeria monocytogene* such as *L. monocytogenes* LSD 15, LSD 332, LSD 336, LSD 338, LSD 339, LSD 340, LSD 341, LSD 346 LSD 348, LSD 523, LSD 524, LSD 525, LSD 526, LSD 529, LSD 530, LSD 531, LSD 532, LSD 535, LSD 538, ATCC 19111, ATCC 19112, ATCC 19114, ATCC 19115 or ATCC 35152, which can be obtained from the Laboratory Services Division Canadian Food Inspection Agency (Ottawa, ON, Canada) or the American Type Culture Collection (Rockville, Md., USA). Moreover, divergicin M35 is effective toward *L. seeligeri, L. welshimeri, L. grayi, L. murayi, L. innocua, Carnobacterium divergens* (ATCC 385) and *Carnobacterium piscicola* (ATCC 386). A skilled artisan will undertstand that divergicin M35 may kill or inhibit the proliferation of several other species of microorganisms.

A further embodiment of the present invention is to provide a nucleic acid encoding an amino acid sequence corresponding to SEQ. ID. NO.1, a functional fragment thereof or a functional variant thereof. A functional fragment of divergicin M35, as intended for the purpose of the present invention, comprises any polypeptide, shorter that the native divergicin M35 but retaining a substantial activity thereof, and more specifically an inhibition activity toward bacteria. Alternatively, a polypeptide may comprise the same number of amino acids as the native divergicin M35 but with a slight modification of the identity of the amino acids and maintain its functionality toward microorganisms. Such a polypeptide is considered as a functional variant of divergicin M35 and is embodied herein. A functional variant as intended herein comprises any polypeptide that differs from SEQ. ID. NO. 1 either by substitution, deletion and/or insertion of one or multiple amino acids, but which substantially retains the antimicrobial activity of the wild-type divergicin M35. For example, a functional variant according to the present invention may comprise substituted amino acids as belong to the same class of amino acids than corresponding amino acids of SEQ. ID. No:1 or amino acids belonging to a different class. Preferably, a functional variant according to the present invention shows at least eighty percent homology with SEQ. ID. NO:1. Alternatively, a functional fragment of divergicin M35 may also comprise variant amino acids while retaining its functionality toward bacteria and a skilled artisan will understand that such a functional variant fragment of divergicin M35 would be an object of the present invention.

In a further embodiment of the present invention, there is provided the use of an affective amount of a divergicin M35, or of a bacteria producing the same, to kill a microorganism or limit its proliferation. The microorganism preferably belongs to the *Listeria* genus, and more preferably to the *Listeria monocytogenes* species. An effective amount of divergicin M35, or of bacteria producing divergicin M35, may find uses in killing a microorganism or limiting its proliferation for example in food, such as smoked salmon, or beverages.

In a further embodiment of the present invention, there is provided a composition for killing a microorganism or limit its proliferation. The composition comprises an effective amount of a divergicin M35 in association with a carrier. Alternatively, the composition of the present invention comprises an effective amount of a bacteria producing divergicin M35 in association with a carrier. The choice of carriers is of course entirely left to one skilled in the art.

Another embodiment of the present invention is to provide a method for producing the bacteriocin of the present invention that comprises cultivating a microorganism producing the bacteriocin, a functional fragment or a functional variant thereof. The cultivated microorganism is preferably a bacteria, that may be a wild-type bacteria or a genetically-modified bacteria, for example the species *Carnobacterium divergens* M35.

The present invention will be more readily understood by referring to the following examples which are given to illustrate the invention rather than to limit its scope.

EXAMPLE 1

Cell Culture

Bacterial strains used for growth inhibition studies are listed in Table 1. Bacteria stocks were maintained as 20% glycerol stock, at −80° C., for further use. *Carnobacterium* sp. and *Lactococcus* sp. strains were cultivated in MRS broth comprising 0.1% (vol/vol) Tween 80® in aerobic condition at 30° C., as currently known in the art. *Listeria monocytogenes* and *Escherichia coli* were grown in tryptic soy broth (TSB), supplemented with 0.6% (wt/vol) yeast extract in aerobic conditions, at 37° C., while *Listeria innocua* and *L. ivanovii* were re-cultivated in TSB with yeast extract and incubated aerobically at 30° C. *Streptococcus thermophilus, Propionibacterium* sp. and pediococci were activated in MRS broth at 37° C. under aerobic condition. All lactobacilli and bifidobacteria were grown in MRS broth supplemented with 0.05% (wt/vol) L-cysteine-hydrochloride and incubated anaerobically in Oxoid jars using an atmosphere generation system, at 37° C. In prior experiments, bacteria strains were sub-cultured at least three times (1%, vol/vol) in respective media at 24 h intervals.

TABLE 1

Reference bacterial strains used in this study.

| Organism | Strain | Sensitivity to divergicin M35 | Diameter of inhibition zone (mm) |
|---|---|---|---|
| *Listeria monocytogenes* | LSD*[a] 15 | − | NA |
| *L. monocytogenes* | LSD 332 | + | 18.5 ± 1 |
| *L. monocytogenes* | LSD 336 | + | 16.5 ± 0.5 |
| *L. monocytogenes* | LSD 338 | + | 18.0 ± 0.5 |
| *L. monocytogenes* | LSD 339 | + | 19.0 ± 0.5 |
| *L. monocytogenes* | LSD 340 | + | 17.0 ± 0.5 |
| *L. monocytogenes* | LSD 341 | + | 13.0 ± 0.5 |
| *L. monocytogenes* | LSD 346 | + | 17.5 ± 1 |
| *L. monocytogenes* | LSD 348 | + | 17.5 ± 1 |
| *L. monocytogenes* | LSD 523 | + | 10 ± 1[b] |
| *L. monocytogenes* | LSD 524 | + | 22.0 ± 1[b] |

TABLE 1-continued

Reference bacterial strains used in this study.

| Organism | Strain | Sensitivity to divergicin M35 | Diameter of inhibition zone (mm) |
|---|---|---|---|
| L. monocytogenes | LSD 525 | − | NA |
| L. monocytogenes | LSD 526 | + | 21.0 ± 1 |
| L. monocytogenes | LSD 529 | + | 14.5 ± 0.5 |
| L. monocytogenes | LSD 530 | + | 19.0 ± 1 |
| L. monocytogenes | LSD 531 | + | 18.5 ± 1 |
| L. monocytogenes | LSD 532 | + | 20.0 ± 0.5[b] |
| L. monocytogenes | LSD 535 | + | 19.0 ± 0.5 |
| L. monocytogenes | LSD 538 | + | 20.0 ± 0.5 |
| L. monocytogenes | ATCC*[b] 19111 | + | ND |
| L. monocytogenes | ATCC 19112 | + | ND |
| L. monocytogenes | ATCC 19114 | + | ND |
| L. monocytogenes | ATCC 19115 | + | ND |
| L. monocytogenes | ATCC 35152 | + | ND |
| L. seeligeri | LSD 11 | + | 13.5 ± 1 |
| L. welshimeri | LSD 12 | + | 20 ± 0.5 |
| L. grayi | LSD 13 | + | 15.0 ± 1 |
| L. murayi | LSD 14 | + | 17.5 ± 1 |
| L. ivanovii | ATCC19119 | − | NA |
| L. ivanovii | HPB*[c]28 | + | ND |
| L. innocua | HPB13 | + | 21 ± 0.5 |
| Carnobacterium divergens | ATCC 385 | + | 15.0 ± 1 |
| Carnobacterium piscicola | ATCC 386 | + | 17.5 ± 1 |
| Lactococcus lactis (subsp. lactis) | R*[d]0058 | − | NA |
| Lactococcus lactis (subsp. lactis biovar. diacetylactis) | R 0100 | − | NA |
| Lactococcus lactis (subsp. lactis biovar. diacetylactis) | UL*[e]719 | − | NA |
| Pediococcus acidilactici | UL 5 | − | NA |
| Pediococcus acidilactici | R 1001 | − | NA |
| Pediococcus pentosaceus | R 1044 | − | NA |
| Lactobacillus salivarius | R 0078 | − | NA |
| Lactobacillus delbrueckii subsp. lactis | R 0187 | − | NA |
| Lactobacillus acidophilus | R 0052 | − | NA |
| Lactobacillus plantarum | R 1012 | − | NA |
| Lactobacillus casei | R R0256 | − | NA |
| Lactobacillus rhamnosus | R 0011 | − | NA |
| Streptococcus thermophilus | R 0083 | − | NA |
| Propionibacterium sp. | P5 | − | NA |
| Propionibacterium freudenreichii | R 0501 | − | NA |
| Bifidobacterium breve | ATCC 15700 | − | NA |
| Escherichia coli 43 | | − | NA |
| Escherichia coli 22 | | − | NA |

*[a]LSD: Laboratory Services Division Canadian Food Inspection Agency (Ottawa, ON, Canada),
*[b]ATCC: American Type Culture Collection (Rockville, MD, USA).
*[c]HPB: Health Protection Branch (Health and Welfare Canada, Ottawa, ON, Canada).
*[d]R: Rosell Institute Inc. (Montreal, PQ, Canada).
*[e]UL: STELA Dairy Research Center Culture Collection (Université Laval, Québec, PQ, Canada).
+, inhibition;
−, no inhibition.
NA, not applicable.
ND, not determined.

EXAMPLE 2

Isolation of Bacteriocin-producing LAB from Seafood

Frozen smoked mussels, smoked salmon and brined shrimps commercially available as frozen packages in the town of Gaspé, Canada during summer season, were obtained. Twenty (20) samples were obtained from each product and were thawed and kept for maturation at 5° C. for 2–8 weeks. Samples were diluted ten-fold with refrigerated 0.1% peptone (wt/vol) and homogenized for 3 minutes in a LAB blender 80 stomacher. Appropriate dilutions were spread-plated on MRS agar medium and incubated at 30° C. for 48 hour periods. Well defined individual colonies were partially removed from plates to inoculate 3 ml of APT broth, further incubated at 30° C. for 18 hour periods.

The obtained isolates were screened for their antilisterial activity using the agar spot method as known in the art, but with some modification. Briefly, 2 μl of an overnight culture of isolate was spotted on a APT agar plate supplemented with 0.6% (wt/vol) yeast extract (APT-YE) and kept at room temperature for 30 min to allow drying. Spots of the same isolated culture were made on five different plates, each plate being used to test individually Listeria monocytogenes strains ATCC 19111, 19112, 19114, 19115, and 35152. The plates were incubated anaerobically at 30° C. for an 18 hour period to prevent $H_2O_2$ production. Plates were further overlaid with 10 ml of molten brain heart infusion comprising 0.75% (wt/vol) agar, 500 IU/ml catalase, 2% (wt/vol) glycerophosphate, and of $10^5$–$10^6$ cfu/ml seeded of the concentrated L. monocytogenes strain. After a 24 hour aerobic incubation at 30° C., the plates were examined for the presence of clear zones surrounding the inoculated spots, which is indicative of an inhibitory activity toward the L. monocytogenes strain. Isolates that showed a clear zone diameter wider than 10 mm were selected for further experiments.

To confirm the proteic nature of the inhibitory substances produced by the isolated strain, the antagonism assay has been repeated with proteolytic enzymes proteinase-K (EC 3.4.21.14), α-chymotrypsin (EC 3.4.21.1), pronase-E (EC 3.4.24.31) and trypsin (EC 3.4.21.4), all from Sigma (St. Louis, Mo., U.S.A.). The proteolytic enzymes were dissolved in 0.01 M phosphate buffer saline (Sigma) at pH 7.5 to reach a concentration of 10 mg/ml. 2 μl of the dissolved enzymes were spotted on APT-YE plates, 2 mm from the inhibitory isolate spot, following a prior incubation at 30° C. for 18 h. The agar plate was then overlaid with brain heart infusion semi-solid agar media, seeded with tested strain of L. monocytogenes as described hereinabove, after which the presence or absence of inhibitory zone was recorded.

On the basis of the width of the clear zones obtained in deferred antagonism assay, several LAB strains were selected for their potential inhibitory activity against L. monocytogenes. A strain isolated from frozen smoked mussels was surrounded by a clear zone having a diameter larger than 12 mm. This isolated colony was selected since it showed the highest antilisterial activity and was trivially named M35. The inhibitory activity of the M35 colony has been attributed to the production of a proteinaceous inhibitory compound since the inhibitory activity is decreased by proteolytic enzymes such as pronase-E, α-chymotrypsin and proteinase K. However, trypsin showed any effect on the inhibitory activity of C. divergens M35 toward Listeria.

EXAMPLE 3

Determination of the Species of the M35 Isolated Colony

The C. divergens M35 isolate has been morphologically and biochemically characterized, to determine $H_2O_2$ production, oxidase test strips (Oxoid), gas production from glucose in APT broth for up to 10 days, as currently reported in the art. The M35 isolate was also tested for its ability to break down arginine, on Moeller Decarboxylase Agar in the presence of 0.5 and 2.0% (wt/vol) glucose, or 10% (wt/vol) sodium chloride at 45° C. The ability of the tested M35 colony to ferment various carbohydrates was determined by using API 50CH (BioMérieux, Montreal, PQ, Canada), according to the manufacturer's instructions. Lactic acid configuration was determined enzymatically using a D-Lactic/L-Lactic acid enzymatic bioanalysis kit (Boehringer Mannheim Gmbh, Mannheim, Germany). The presence of meso-diaminopimelic acid in the cell wall was tested as currently known in the art. Finally, the capacity of the strain to grow at 5° C. was determined by periodic spread counts on tryptic soy agar (Difco, Detroit, Mich., U.S.A.) of a culture in APT-YE broth maintained at 5° C.

Based on the identification scheme proposed in the background art and the carbohydrate fermentation profile using the API system, the M35 colony was attributed to the *Carnobacterium divergens* species. Indeed, the *C. divergens* M35 strain is Gram positive short rod, catalase and oxidase negative, and produces only L-lactic acid as product of fermentation process accompanied by very weak gas production. This strain is able to grow at 5° C. but not at 45° C., tolerates salt up to 10%, and metabolizes arginine at low glucose concentration of 0.5%, but not at 2.0%. Furthermore, the bacterial stains contains meso-diaminopimelic type peptidoglycan in its cell wall. The API identification procedure resulted in an excellent identification of *Carnobacterium divergens*, except for a doubtful melezitose reaction.

To confirm the genus and species to which M35 strain belong, PCR analyses were performed on DNA extracted from a 1 ml aliquot of an overnight MRS culture of the *C. divergens* M35 isolate, sedimented by centrifugation, washed and re-suspended in sterile water. DNA extraction was performed using a Qiagen DNA purification kit. (Qiagen Inc., Mississauga, ON, Canada), following the manufacturer's instructions. The PCR amplification was performed in 25-μl of a reaction buffer comprising: 1× Taq buffer, 0.5 unit of Taq DNA polymerase, (New England Biolab Inc., Beverly, Mass., USA), 25 ng of each primer, 0.5 μl of bacterial suspension and 0.1 mM of dNTP (Amersham Biosciences, Baie d'Urfé, PQ, Canada). An automated DNA thermal cycler Perkin Elmer Gene Amp PCR system 2400 was used to provide temperature cycle recommended in the art. The PCR Amplification products were visualized on a 3% (wt/vol) agarose gel electrophoresis, stained with 0.5 g/ml ethidium bromide, using a 100-bp ladder as size marker.

Genus-specific primers Cb1f and Cb2r have been used to determine the genus and confirm the genus of the M35 stain. These primers have been previously designed for the genotypic characterization of *Carnobacterium* spp. by DNA amplification. Primers Cb1f and Cb2r were used to amplify a target region of 340 bp within the 16S rDNA of the putative *Carnobacterium* mussels isolate M35.

To confirm the species to which the M35 isolate belongs, a universal forward primer, 27f, and a species-specific forward primer, Cga, were used, in combination with three species-specific reverse primers, Cdi, Cmo and Cpg, previously reported in the art. Forward primer, Cga, is designed to specifically amplify *C. gallinarum* while reverse primers Cdi, Cmo and Cpg are designed to specifically amplify *C. divergens, C. mobile* and *C. piscicola/C. gallinarum* species, respectively. Forward 27f and reverse primers, Cdi, Cmo and Cpg were used to amplify specific target regions of 198–199 bp within the 16S rDNA, while, primers Cga and Cpg were used to amplify a 128 bp region. rDNA from *Lactobacillus farciminis* was used as PCR-amplification negative control reactions. All primers used for PCR analyses were obtained from Invitrogen™ Corporation (Frederick, Md., USA).

PCR analyses to determine the genus of the M35 strain resulted in the specific amplification of a 340 pb fragment from 16S rDNA using *Carnobacterium* genus-specific primers Cb1f and Cb2r (FIG. 1a). PCR amplifications using universal and species-specific primers are shown in FIG. 1b. The 199 pb PCR product expected for *C. divergens* has been obtained from 16S rDNA of strain M35 using 27f-Cdi pair primers. Those results were in accordance with morphological and biochemical tests.

EXAMPLE 4

Purification of Divergicin M35 Bacteriocin

Purification of divergicin M35 was performed following a three-step process developed and optimized in this study. An overnight MRS culture of *C. divergens* M35 was heated in a water bath at 100° C. for 10 min and centrifuged at 7,000 g for 15 min at 4° C. The supernatant was applied to a SP-Sepharose Fast Flow Cation Exchange Column (Amersham, Pharmacia Biotech, Uppsala, Sweden) at a flow rate of 3 ml/min. The exchange column was then washed and equilibrated using 1 liter of ammonium acetate buffer (5 mM, pH 5). Bacteriocin was eluted using 250 ml of 1.5% (wt/vol) sodium chloride diluted in acetate buffer. The eluted bacteriocin was loaded onto a sep-pack Vac $C_{18}$ Cartridge micro-column (Waters, Milford, Mass., USA) previously equilibrated with 5 mM HCl, prepared in HPLC-grade water. Bacteriocin was eluted from the sep-pack using 60 ml of 50% (vol/vol) acetonitrile (VWR International, Montreal, PQ, Canada) prepared in water. Acetonitrile was removed using a rotary evaporator and bacteriocin M35 was concentrated under vacuum with a speed vac concentrator (Thermo Savant Instruments Inc., N.Y., USA) and kept at −80° C.

The concentrated bacteriocin was further purified by Reverse-Phase Column Liquid Chromatography (RP-HPLC) using a Beckman Gold System (Beckman Coulter Canada Inc., Mississauga, ON, Canada). Briefly, 100 μl of the concentrated bacteriocin were injected into an analytic $C_{18}$ reverse-phase column (Luna 5μ, 4.6×250 mm, Phenomenex, Calif., USA). Elution was performed at a flow rate of 1 ml/min using a linear gradient from 90% solvent A (0.1% (wt/vol) trifluoroacetic acid (TFA) prepared in 5% (vol/vol) acetonitrile in water) and 10% solvent B (0.1% TFA in 100% acetonitrile) to 42 and 58% of solvents A and B, respectively, for 46 min. Peptide fractions were detected by spectrophotometry by measuring the absorbance at 220 nm and were collected manually. The fractions were concentrated using a speed-vac concentrator, dissolved in acetate buffer (0.0 M, pH 4.0) and assayed for both bacteriocin activity by the critical-dilution micromethod, and protein content.

Protein concentration was determined as known in the art. Two-fold serial dilutions of 125 μl of tested sample were transferred into wells with a flat bottom microtest™ polystyrene microplate (96-well microtest, Becton Dickinson Labware, Franklin Lakes, N.J., USA), previously filled with 125 μl tryptic soy broth supplemented with 0.6% yeast extract (wt/vol). Each well was inoculated with 50 μl of 1000-fold diluted overnight culture of *L. innocua* HPB13 (final concentration of approximately $10^6$ cfu/ml) and incubated at 30° C. for 18 h. Optical densities (650 nm) were then measured using a Thermo-max molecular device spectrophotometer (OPTI-Resources Inc., Quebec, PQ, Canada). The bacteriocin activity, expressed in arbitrary units per milliliter (AU/ml), was defined as the highest bacteriocin dilution showing complete inhibition of the indicator strain (optical density equals to that in un-inoculated media). The activity was calculated using the formula: AU/ml=$2^n \times$(1000/125) where n is the number of wells, showed inhibition of the indicator strain.

Results of the different purification steps are given in Table 2. The biological activity of divergicin M35 was determined during the purification procedure by both agar diffusion and critical-dilution methods using *L. innocua* HPB 13 as indicator strain. Table 2 and FIG. 2 also shows the activity of divergicin M35 obtained during the different purification steps.

TABLE 2

Divergicin M35, purification steps and Relative activity of bacteriocin, produced with *C. divergens* M35.

| Purification stage | Volume (ml) | Total protein (mg) | Total activity[a] (AU) | Specific Activity[b] (AU/mg) | Increase in specific Activity[c] (fold) | Yield[d] (%) |
|---|---|---|---|---|---|---|
| A (culture supernatant) | 500 | 7 558 | $32.8 \times 10^6$ | $4.3 \times 10^3$ | 1 | 100 |
| B (Sp-Sepharose) | 250 | 625 | $8.2 \times 10^6$ | $13.1 \times 10^3$ | 3 | 25 |
| C (Sep-Pack $C_{18}$) | 60 | 1.43 | $31.5 \times 10^6$ | $22.0 \times 10^6$ | 5 074 | 96 |
| D (RP-HPLC) | 0.8 | $8.2 \times 10^{-2}$ | $3.3 \times 10^6$ | $40.9 \times 10^6$ | 9 438 | 10 |

[a]Activity (AU/ml) was determined by a microtiter plate assay using *L. innocua* HPB13 as indicator microorganism and total activity was calculated as activity (AU/ml) multiplied by the volume in milliliters
[b]Activity (AU/ml) divided by total protein (mg)
[c]Specific activity (AU/mg) at stage $n_i$ divided by specific activity (AU/mg) at stage $n_0$, with stage $n_0$, the supernatant and stage $n_i$, one of the subsequent stage of purification
[d]Total activity (AU) at stage $n_i$ divided by total activity (AU) at stage $n_0$ and expressed as percentage, with stage $n_0$, the supernatant and stage $n_i$, one of the subsequent stage of purification Based on activity measurement, cation-exchange SP-sepharose allowed the recovery of 25% of the bacteriocin activity obtained with the cell-free supernatant and was accompanied with 3-fold increased total specific activity (Table 2). Divergicin M35 eluted from SP-sepharose column with 1.5% sodium chloride was directly applied to a sep-pack $C_{18}$ column for further purification according to its hydrophobic character. Divergicin M35 appeared to be anchored to the column matrix and was easily eluted with 50% (vol/vol) acetonitrile. By comparison with SP-sepharose purification step, sep-pack $C_{18}$ allowed a 96% recovery yield of divergicin M35 initially found in the culture supernatant. Calculated specific activity was 5074-fold higher than that obtained with crude culture supernatant.

Figure 2:
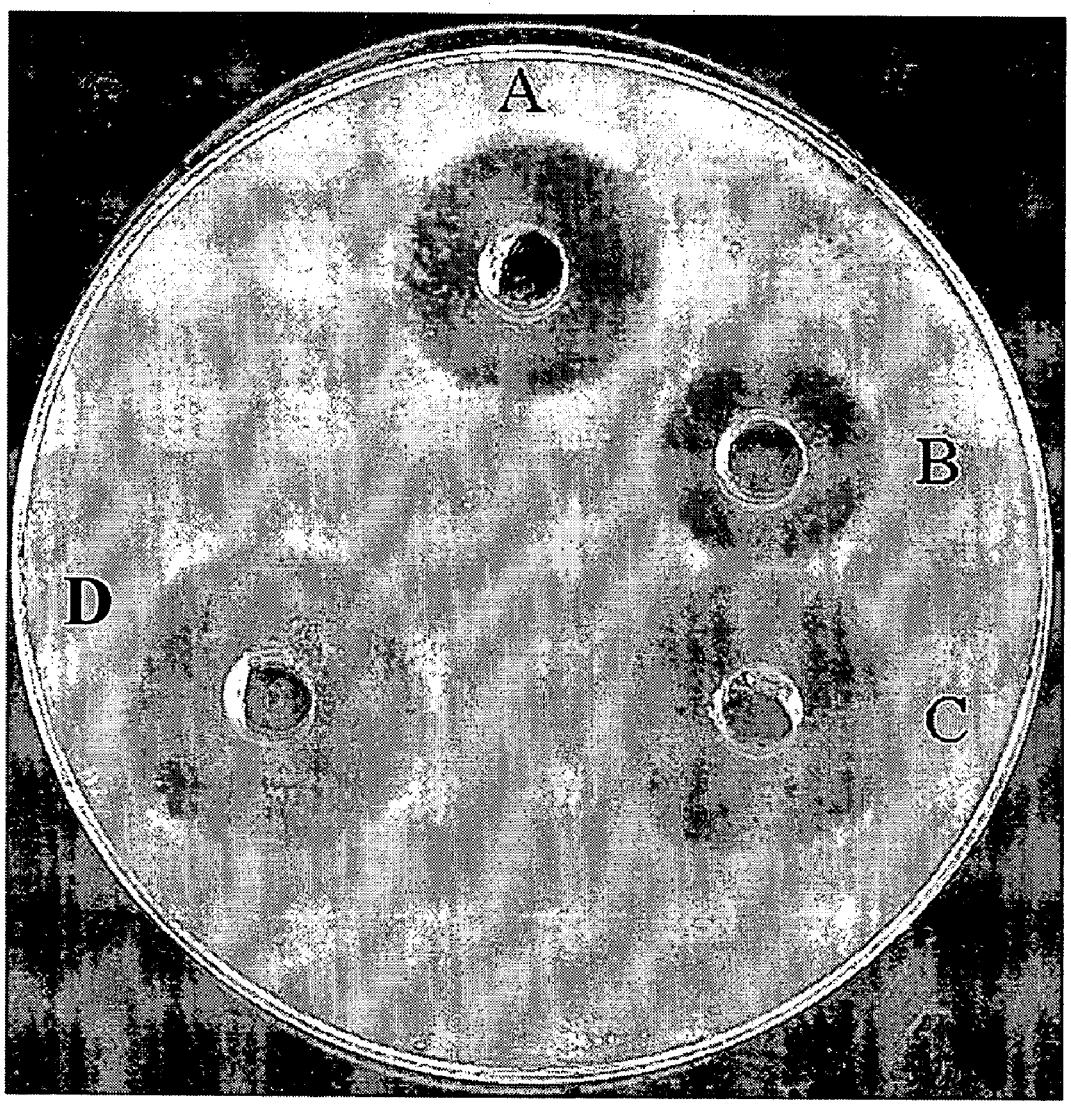
FIG. 2 shows the inhibition of *Listeria innocua* HPB13 by *C. divergens* M35 culture supernatants after each purification steps.
Figure 3:
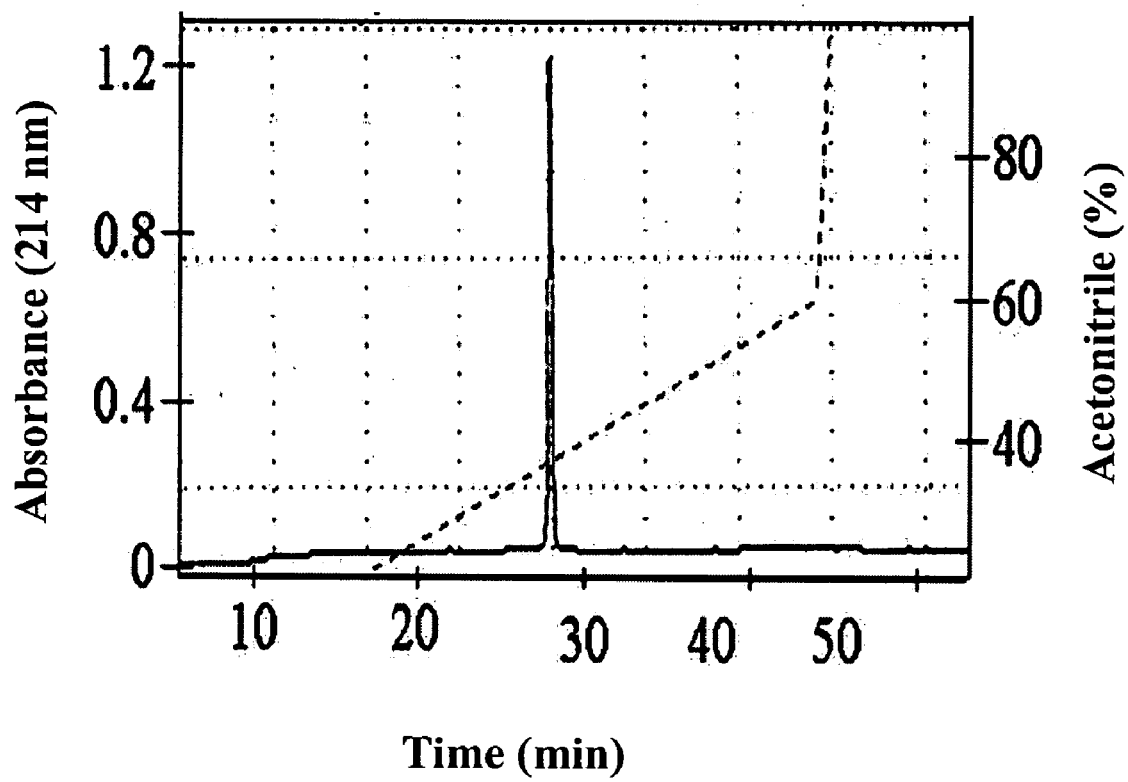
FIG. 3. is a reversed-phase chromatography analysis of a divregicin M35-containing fractions on a $C_{18}$ Nucleosyl column.

Final purification of divergicin M35 was achieved using the reverse-phase $C_{18}$ HPLC system (RP-HPLC). The elution profile monitored at 220 nm showed three distinct peaks eluted at 36.3, 38.6 and 41.6% of acetonitrile, corresponding to retention times of 27.3, 28.6 and 32.6 mm, respectively. Peaks having retention times of 27.3 and 28.6 mm were shown to be active against *L. innocua* HPB 13, as shown in FIG. 2, while peak eluted at 32.6 mm was inactive toward this microorganism. The major peak showing antibacterial activity (retention time 28.6 mm) was recovered, re-injected onto the HPLC (FIG. 3) to assess its purity and was further subjected to mass and amino acid sequencing analyses. A second HPLC separation has increased the specific activity of divregicin M35 by 9500-fold higher compared to the activity of crude supernatant. Recovery yield was 10% of the total bacteriocin found in crude supernatant.

EXAMPLE 5

Mass and Amino Acid Sequence of Divergicin M35

Amino acid sequence was determined by Edman degradation on an automated sequencer (model 492; Applied biosystems) in Sheldon Biotechnology Centre (McGill University, Montreal, PQ, Canada). Mass determination was performed using a Voyager De matrix assisted laser desorption ionisation-time of flight (MALDI-TOF) mass spectrometer with an accuracy of ±0.02%. The HPLC-purified peptide was mixed (1:1, vol/vol) with the MALDI-TOF matrix on a gold plated plate. The matrix was a saturated solution of $\propto$-cyano-4-hydroxycinnaminic acid (97%, F.W. 189,17; Aldrich) comprising 50% acetonitrile and 0.1% TFA. Protein homology search (SWALL and SWISS-PROT) and sequence analysis were performed with the ExPASy proteomics tolls sequence analysis software package.

Figure 4:
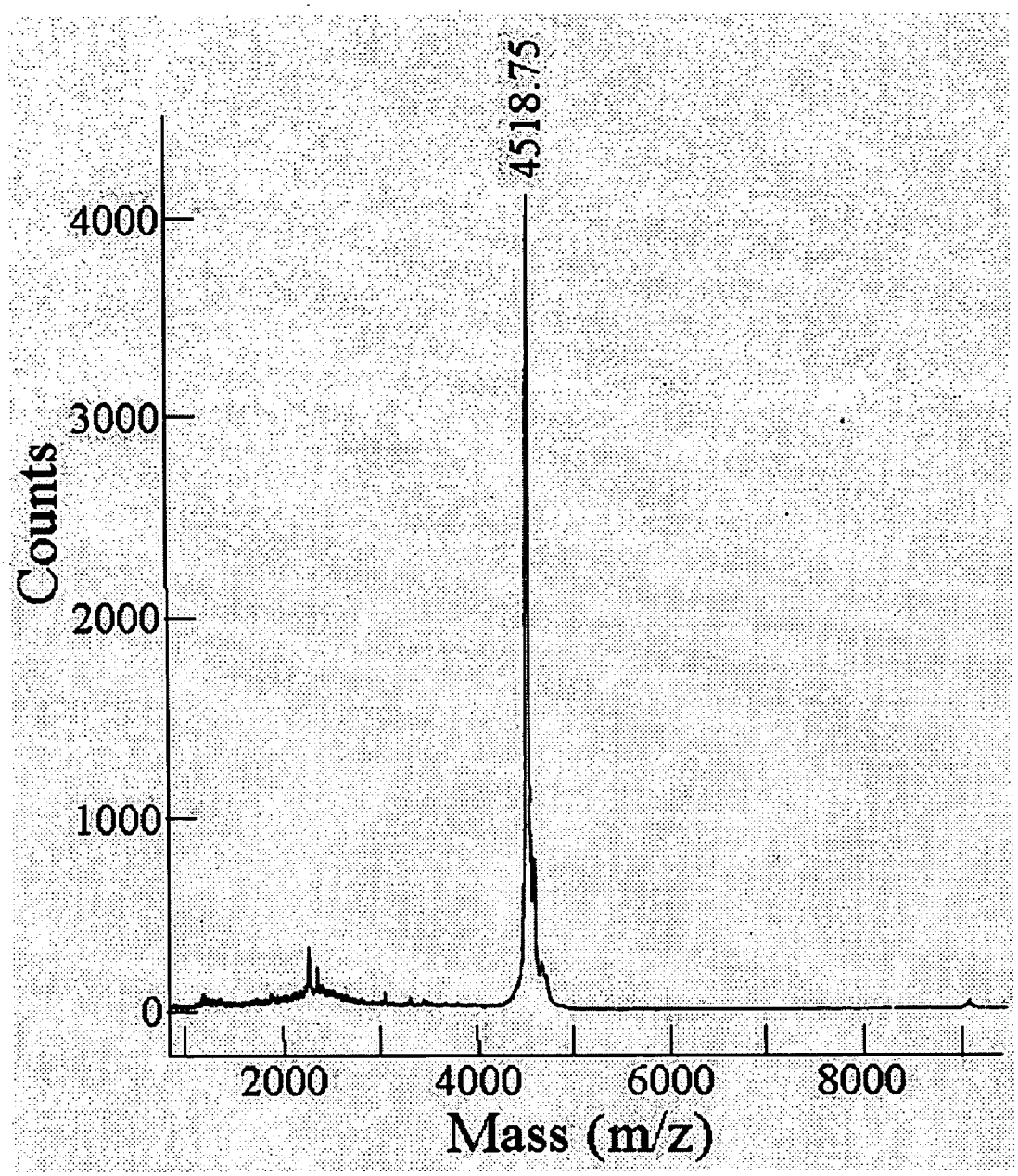
FIG. 4 is a mass spectrometry analysis of divergicin M35.

The HPLC-purified peptide analyzed by mass spectrometry showed a molecular mass of approximately 4518.75 Da (FIG. 4). Amino acid sequencing demonstrated a 43 amino acid peptide comprising four cysteine residues, at position 10, 15, 25 and 43 (Table 3). Divergicin M35 (SEQ ID NO: 1) shows a variable degree of homology with other class IIa bacteriocins including divercin V41 (80.5%) (SEQ ID NO: 2) bavaricin MN (80%) (SEQ ID NO: 3), enterocin A (61%) (SEQ ID NO: 4), mundticin (51.2%) (SEQ ID NO: 5) and enterocin P (50%) (SEQ ID NO: 6). The highest sequence similarity with other class IIa bacteriocins, was observed in the N-terminal halves with the presence of the motif YGNGVXaaCXaaXaaXaaXaaXaaCXV(D/N)(G/A/S)XaaA (SEQ ID NO:7) (amino acid residues with low variability are inside brackets, residues in capitals can be replaced with residues in lowercase, and those with higher variability are represented by Xaa). As a common feature of all class IIa bacteriocins, divergicin M35 is characterized by a high content of non-polar amino acid residues (32.6%) and small amino acids such as glycine (23%). The net positive charge (+3) of divergicine M35 results from the presence of two residues of asparagine ($Asp_{18,27}$) and five lysines ($Lys_{2, 13, 14, 40, 42}$). Divergicin M35 has a calculated PI value of 8.6.

TABLE 3

Amino Acid Sequence of Divergicin Met

| Bacteriocin | Amino acid sequence | |
|---|---|---|
| Divergicin M35 (100%) | TKYYGNGVYCNSKKCWVDWGIAQGCID--VVIGQLGGGLPGKGKC | (SEQ ID NO: 1) |
| Divercin V41 (80.5%) | TKYYGNGVYCNSKKCWVDWGQASGCIGQTVVGGWLGGAIPGL-KC | (SEQ ID NO: 2) |
| Bavaricin MN (80.0%) | TKYYGNGVYCNSKKCWVDWGQAAGGIGQTVVXGWLGGAIPGFIK | (SEQ ID NO: 3) |
| Enterocin A (61.0%) | TTMSGKYYGNGVYCTKNKCTVDWAKATTTCIAGMSIGGFLGGAIPGKC | (SEQ ID NO: 4) |
| Mundticin (51.2%) | KYYGNGVSCNKKGCSVDWGKAIGIIGNNSAANLATGGAAGWSK | (SEQ ID NO: 5) |
| Enterocin P (50.0%) | ATRSYGNGVYCNNSKCWVNWGHAKENIAGISGWASGLAGM-GH | (SEQ ID NO: 6) |

EXAMPLE 6

Characterization of Divergicin M35 Activity

The antibacterial activity of bacteriocin produced by *C. divergens* M35 was tested toward a variety of bacteria species, listed in Table 1, and belonging to genus *Listeria, Lactobacillus, Streptococcus, Lactococcus, Propionibacterium* and *Escherichia*, and was evaluated following the agar diffusion method, as is well known to those skilled in the art.

The spectrum of activity of divergicin M35 was examined against several food isolates of *Listeria monocytogenes* and some lactic acid bacteria, as shown in Table 1. Divergicin demonstrated higher specificity to inhibit *L. monocytogenes*. Of the 24 tested strains of *L. monocytogenes*, 22 appeared sensitive to divergicin M35 and showed diameters of inhibition zones that vary from 10 to 22 mm. The two strains, *L. monocytogenes* LSD 15 and 525, were resistant. Divergicin M35 has antibacterial activity against other species of genus *Listeria* including *L. ivvanovi, L. innocua, L. seeligeri, L. welshimeri, L. grayi* and *L. murayi*. In every case, the antibacterial activity of divergicin M35, determined in term of the diameter of the inhibition zone, remained stable at least for 36 h. Moreover, divergicin M35 shows antibacterial activity against closely related bacteria *C. divergens* and *C. piscicola* (Table 1), but cannot inhibit strains belonging to genus *Lactobacillus, Lactococcus, Streptococcus, Pediococcus, Propionibacterium* and *Bifidobacterium*. Gram-negative strains tested belonging to *Escherichia coli* were not affected by divergicin M35.

The thermal stability of divergicin M35 has also been determined. MRS culture of *C. divergens* M35 at late exponential phase was centrifuged at 7000 g for 20 min. The supernatant was heated at 100° C. for 30 and 60 min or at 121° C. for 20, 30 and 60 min. Bacteriocin activity was determined by the agar diffusion method, using *L. innocua* HPB29.

The fluid MRS supernatant of *C. divergens* M35 retains a considerable part of its activity after high temperature treatments, as determined by the agar diffusion method using *L. inncoua* HPB13 as target organism. Compared to unheated supernatant, the width of the inhibition zone was reduced by 50, 75 and 78.5%, respectively, when the supernatant treated at 121° C. for 10, 20 and 30 min.

EXAMPLE 7

Growth of *C. divergens* M35

A *C. divergens* M35 culture were diluted (1% vol/vol) in peptone water (0.1%), plated on MRS agar supplemented with 0.1% vol/vol Tween 80® and incubated aerobically at 30° C. for 24 h. Bacterial viable counts, bacteriocin activity and pH were determined at 2 h intervals. Bacteriocin activity was determined according to the critical-dilution micromethod described hereinabove, using 5 ml of culture supernatant, separated by centrifugation and heated at 100° C.

Figure 5:
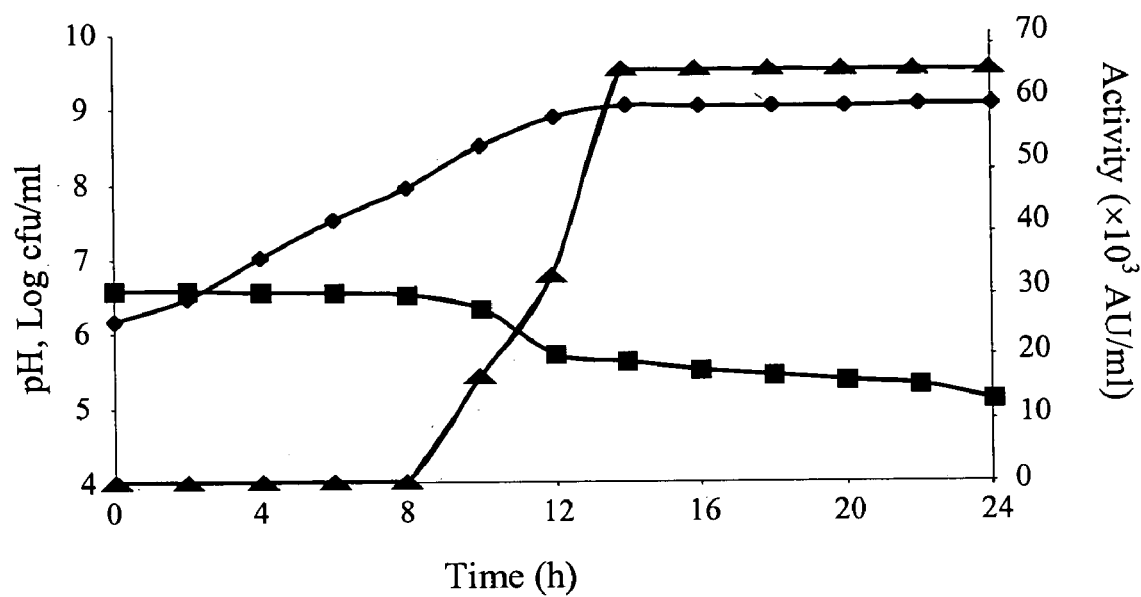
FIG. 5 shows the growth and acid production of *Carnobacterium divergens* M35 and divergicin M35 activity in MRS broth at 30° C.

As shown in FIG. 5. *C. divergens* M35 grows to a satisfactory rate in MRS broth and the maximum of cellular mass of approximately log 9 cfu/ml can be reached after 12 h of incubation at 30° C. which is the end of the exponential growth phase, and remained relatively stable during the next 12 h. The production of divergicin M35 begins during the late stage of exponential phase of growth of *C. divergens* M35 cultivated in MRS-containing Tween 80® (FIG. 5). The biological activity of divergicin M35 is detected after 10 h of growth (approximately 18000 AU/ml), and continued to produce to reach a maximum of 65000 AU/ml after 14 h of growth, which corresponds to the beginning of the stationary growth phase. The activity remains stable during the extended 12 h of incubation time of the stationary phase. A slight decrease in the pH value was observed during the growth of *C. divergens* M35. Acid production appears to be growth-associated metabolite since the lowest values were observed at the end of the exponential growth phase, the pH dropping from 6.6 to 5.5 and remaining relatively stable during the stationary phase.

EXAMPLE 8

Inhibition of *L. monocytogenes* Proliferation by *C. divergens* M35 in Food Products To determine the effect of the presence of *C. divergens* M35 on the proliferation of pathogenic bacteria in food products, smoked salmon have been inoculated with *L. monocytogenes*, in the presence or absence of *C. divergens* M35, and the number of colony forming units (CFU) per gram of smoked salmon was monitored for *L. monocytogenes* and total LAB.

Briefly, smoked salmon have been inoculated at day 0 with y 5×10³ cells of *L. monocytogenes* alone (control), or in combination with 5×10³ cells of *C. divergens* M35. The inoculated smoked salmon was stored at 4° C. in vacuumed sealed bags for a 28-days period, during which proliferation of *L monocytogenes* and total LAB was monitored, using the methods known in the prior art.

Figure 6:
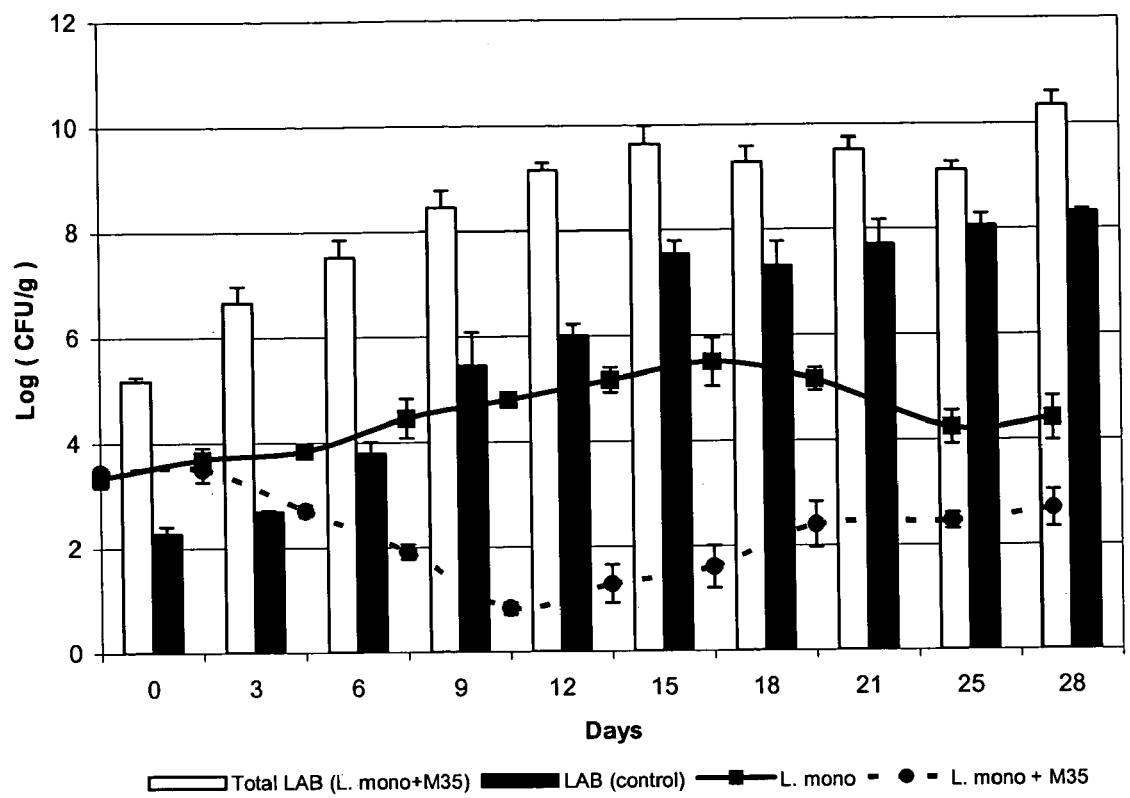
FIG. 6 shows the proliferation of *L. monocytogenes* and total LAB in the presence or absence of *C. divergens* M35.

FIG. 6 shows that the presence of *C. divergens* M35 reduced the concentration of *L. monocytogenes* by approximately 2.5 log per gram of smoked salmon, when compared to the concentration of *L. monocytogenes* in control sample. The decrease in *L. monocytogenes* count in smoked salmon started at day 3, and remains lower for the whole experimentation period,compared to day 0. These results show that *C. divergens* M35 inhibits the proliferation of pathogenic bacteria found in food products and that *C divergens* M35 or the bacteriocin produced therefrom can be used as preservative agents.

A deposit of the bacteria producing SEQ ID NO: 1 according to the present invention has been made under the provision of the Budapest Treaty, at the International Depositary Authority of Canada (1015 Arlington street, room H5190, Winnipeg, Manitoba, R3E 3R2) on Apr. 5, 2004. The deposit number is 050404-01.

While the invention has been described in connection with specific embodiments thereof, it will be understood that it is capable of further modifications and this application is intended to cover any variations, uses, or adaptations of the invention, following, in general, the principles of the invention, and including, such departures from the present disclosure as come within known or customary practice within the art to which the invention pertains and as may be applied to the essential features hereinbefore set forth, and as follows in the scope of the appended claims.

We claim:

1. A purified bacteriocin that comprises the amino acid sequence of SEQ. ID. NO: 1, wherein said bacteriocin presents an antimicrobial activity towards a bacteria of the *Listeria* genus.

2. A composition for killing a bacteria of the *Listeria* genus or limiting its proliferation that comprises (i) an effective amount of a purified bacteriocin and (ii) a carrier, wherein said purified bacteriocin comprises the amino acid sequence of SEQ. ID. NO: 1.

3. A method for killing a bacteria of the *Listeria* genus or limiting its proliferation by adding an affective amount of a purified bacteriocin that comprises the amino acid sequence of SEQ ID NO: 1 to said bacteria of the *Listeria* genus.

4. The method according to claim 3, wherein said bacteria of the *Listeria* genus belongs to the *Listeria monocytogenes* species.

5. The method according to claim 3, wherein said bacteria of the *Listeria* genus is a food product.

6. The method according to claim 5, wherein said food product is smoked salmon.

* * * * *